United States Patent [19]

Bonito

[11] Patent Number: 4,718,902
[45] Date of Patent: Jan. 12, 1988

[54] ENDOMETRIOSIS PANTY

[76] Inventor: Ruth Bonito, 29 Heather La., Windsor Locke, Conn. 06096

[21] Appl. No.: 861,277

[22] Filed: May 9, 1986

[51] Int. Cl.⁴ .............................................. A61F 13/16
[52] U.S. Cl. .................................................... 604/396
[58] Field of Search ...................... 604/396, 397, 385.1, 604/365, 370, 382

[56] References Cited

U.S. PATENT DOCUMENTS

| | | | |
|---|---|---|---|
| 3,098,484 | 7/1963 | Younger | 604/396 |
| 3,237,625 | 3/1966 | Johnson | 604/396 |
| 3,368,563 | 2/1968 | Scheier | 604/396 |
| 3,461,872 | 8/1969 | McConnell et al. | 604/397 |
| 3,613,687 | 10/1971 | Kennedy | 604/396 |
| 3,828,785 | 8/1974 | Gamm et al. | 604/397 |
| 4,244,367 | 1/1981 | Rollenhagen | 604/396 |
| 4,351,340 | 9/1982 | McLeod | 604/396 |
| 4,352,356 | 10/1982 | Tong | 604/397 |
| 4,560,381 | 12/1985 | Southwell | 604/396 |

Primary Examiner—John D. Yasko
Attorney, Agent, or Firm—Lawrence Hager

[57] ABSTRACT

A panty construction including an interior liquid absorbent layer. The liquid absorbent layer comprises a flexible vinyl-coated terry cloth fabric having a panel extending from the front waist through the crotch to the back waist band of the panty. The panel is stitched into the panty with an overcast stretch stitch.

3 Claims, 5 Drawing Figures

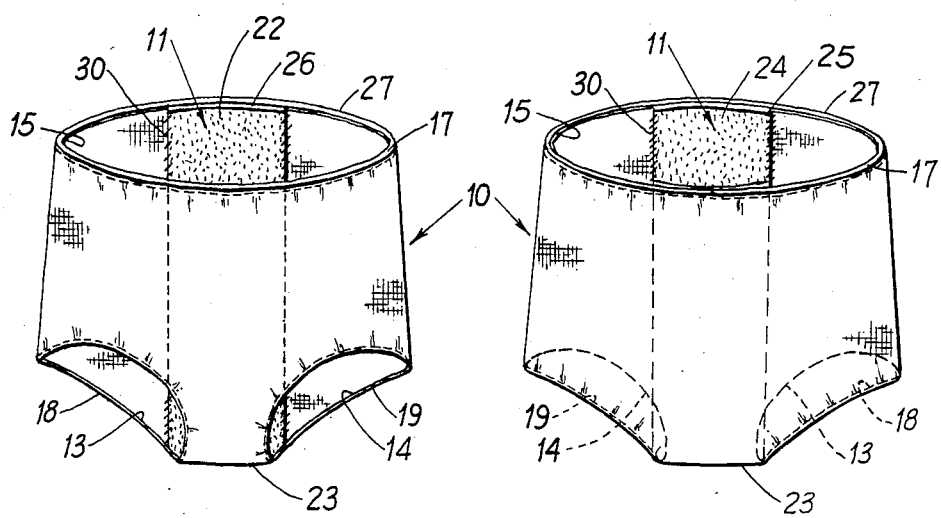
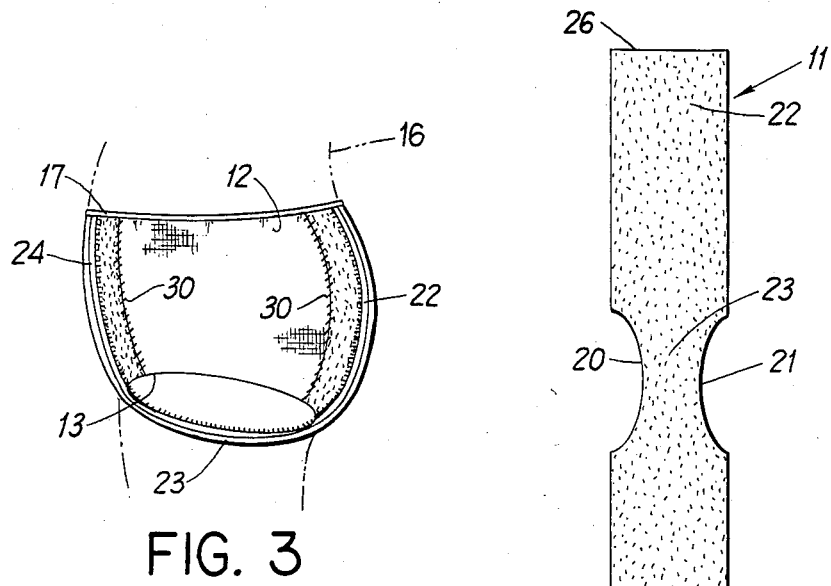
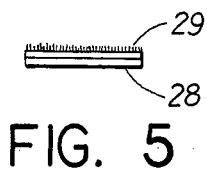

ENDOMETRIOSIS PANTY

FIELD OF THE INVENTION

The present invention relates to a panty or undergarment and, more particularly, to a unique construction for a panty having an inner absorbent layer.

BACKGROUND OF THE INVENTION

Various types of panty constructions have hitherto been proposed such as a panty liner construction as described in U.S. Pat No. 4,351,340 issued Sept. 28, 1982 to Syble A. McLeod. This patent reference basically shows and describes a diaper like panty liner or insert having a partial front panel which does not extend to the waist opening.

Another prior art panty is shown in U.S. Pat. No. 4,352,356 issued Oct. 5, 1982 to David P. Tong. This patent again shows an internal pouch and absorbent pad which does not extend to the waist opening.

Another prior art panty liner construction is shown in U.S. Pat. No. 4,227,531 issued Oct. 14, 1980 to Syble A. McLeod. This patent reference also shows a diaper like panty liner having a partial front panel which does not extend to the waist opening.

Yet another prior art diaper cover type garment is shown in U.S. Pat. No. 4,241,462 issued Dec. 30, 1980 to Hiroshi Tagawa et al. This patent shows an open type diaper and does not show or describe a panty.

The above noted patents are mentioned as being representative of the prior art and other pertinent references may exist. None of these patents are deemed to affect the patentability of the present claimed invention.

In contrast to the prior art, the present invention provides a panty with a panel extending from the waist, both front and back, having a special stain resistant and liquid proof insert. The panel is stitched into the panty garment with an overcast or other stretch stitch to round edge of insert to improve flexibility and wearing comfort. The insert is composed of a thin, very soft, flexible vinyl backed terry cloth fabric. The terry cloth faces the skin of a user to prevent skin contact with the vinyl plastic and does not interfere with the use of tampons or sanitary napkins. The vinyl coating substantially prevents leakage and staining problems. The nature of the vinyl backed terry cloth fabric is such that it does not add appreciable bulk to the panty and thus does not interfere with the appearance of feminine outer wear such as tight fitting dresses, skirts, trousers and the like.

SUMMARY OF THE INVENTION

Generally speaking, in accordance with the invention, a panty (construction) is provided having particular utility for convenient, relatively inexpensive, comfortable and relatively inconspicuous wear, for substantially preventing menstrual flow from staining outer garments or clothing, comprising:

a panty or female underwear having a waist opening at its top and a pair of leg openings at its bottom; and a panel assembly including a front section, a back section and a crotch section joining the front and back sections, said back and front sections each extend from said crotch section up to the waist opening of said panty, said panel assembly being stitched into said panty with an overcast or other type of stretch stitch to improve flexibility and wearing comfort, said panel assembly being formed of a vinyl backed terry cloth fabric.

Accordingly, it is an object of the present invention to provide a new and improved panty construction.

Another object of the present invention is to provide a new and improved panty liner construction.

Another object of the present invention is to provide a panty liner having a front and a rear panel extending to the waist of the panty.

Another object of the present invention is to provide a panty having a flexible, liquid-proof sheet extending from the front panty waist through the crotch and to the rear panty waist.

Another object of the present invention is to provide a panty having a liner formed of a vinyl backed terry cloth fabric.

Another object of the present invention is to provide a panty construction having a liquid-proof terry cloth backed liner stitched into the panty with stretch stitch.

Another object of the present invention is to provide a relatively inexpensive panty with affixed liner for preventing menstrual flow leakage to outer garments.

Another object of the present invention is to provide a panty liner which will not induce unnecessary perspiration.

Another object of the present invention is to provide a panty for relatively comfortable and inconspicuous use during menstrual periods.

Another object of the present invention is to provide a panty for preventing staining of bedding during sleep periods for women with endometriosic conditions (over 25% of female population wherein unusually heavy menstrual flow may occur during sleep periods).

Another object of the present invention is to provide a panty for preventing staining of garments, bedding, and the like after D&C's or other surgery.

BRIEF DESCRIPTION OF THE DRAWINGS

Other objects and advantages of the invention may be more clearly seen when viewed in conjunction with the accompanying drawings. Similar reference numerals refer to similar parts throughout.

FIG. 1 is a front view, partly in phantom outline, of the menstrual panty constructed in accordance with the invention;

FIG. 2 is a rear view, partly in phantom outline, of the menstrual panty shown in FIG. 1;

FIG. 3 is a perspective cross-sectional view of the menstrual panty according to the invention;

FIG. 4 is a folded out view of the menstrual panty liner in accordance with the invention; and FIG. 5 is a perspective end view of the menstrual panty liner shown in FIG. 4.

DESCRIPTION OF THE PREFERRED EMBODIMENT

Referring to the drawings it will be seen that the preferred embodiment of the invention basically comprises a conventional type panty 10 having a novel panty liner 11 for either frill panty or bikini types as well as for lace types with definite feminine appeal.

The panty 10 generally has an interior surface or lining 12 and a pair of leg openings 13 and 14 at its lower portion and a waist opening 15 at its upper portion to enable the panty 10 to be worn by a user 16 (partly shown in phantom outline).

The panty 10 may be formed of fabric such as cotton, silk or other suitable material. An elastic band 17 of conventional design may be stitched about the panty waist opening 15 to provide a snug fit about the waist of the wearer 16. Similarly, an elastic band 18 and 19 may be stitched about each leg opening 13 and 14, respectively, to provide a snug fit about the legs of the wearer 16.

The panty liner 11 comprises a flexible vinyl layer or coating 18 and a layer or coating of terry cloth 19 which is affixed to vinyl layer 18. Panty liner 11 may be of rectangular configuration with a pair of concave notches 20 and 21, which are contoured to fit in juxtaposition about a leg opening 13 and 14 (and/or elastic band 18 and 19), respectively. Panty liner 11 incorporates a back portion 22, a crotch portion 23 and a front portion 24. The back portion 22 extends from the waist opening 15 or waist band 17 down to the crotch portion 23. The front portion 24 extends from the waist opening 15 or waist band 17 down to the crotch portion 23. As best seen in FIGS. 1 and 2, both the front portion 24 and the rear portion 22 each have an upper edge 25 and 26, respectively, in juxtaposition and parallel to the edge 27 of the waist opening 15. The panty liner 11 is stitched into the panty 10 with an overcast stretch stitch 30 to improve flexibility and wearing comfort. The vinyl layer 18 is placed in contact with the inner lining 15 of panty 10, while the terry cloth layer 19 provides an absorbent and comfort layer against the wearer's body 16. Thus, the terry cloth 19 is in contact with the skin for comfortable wear, and yet panty liner 10 is relatively thin so as not to interfere with the use of tampons and/or external sanitary napkins (not shown). The relatively high front and back portions 24 and 22 were discovered to provide improved protection from menstrual flow leakage from without panty liner 10.

In accordance with the preferred embodiment of the invention, a flexible vinyl backed terry cloth known by the name or trademark SYNTILON, available from Pervel Industries, Inc. located at Plainfield, Conn., is utilized as a panty liner 11. The SYNTILON material is generally made by a process of (1) casting the flexible vinyl plastiol onto a transfer paper and then, (2) applying the terry cloth to the vinyl by reverse rollar costing under very low pressure, and (3) fusing the vinyl/terry cloth together in an oven. This process results in a minimum impregnation of the terry cloth with the vinyl to produce a very flexible, non-boardy composite. In contrast to the conventional application by spreading the flexible vinyl mix directly on the fabric.SYNTILON is the trademark of a product particularly suited for a purpose since it has incorporated into its composition fungicides and bacteriostat which are not removed or reduced by repeated laundry.

Thus, this invention utilizes a new use of a specific vinyl backed terry cloth to resolve prior art problems and to meet a long felt yet unresolved need in a relatively economical manner. Accordingly, the term flexible vinyl-coated terry cloth fabric or vinyl backed terry cloth hereinafter shall mean the above SYNTILON type material and any substantially similar or equivalent thereto.

While there has been shown what is considered to be the preferred embodiment of the invention, it is desired to secure in the appended claims all modifications as fall within the true spirit and scope of the invention.

I claim:

1. A panty for use by a woman during a menstrual flow period and by a person with an incontinence problem, comprising:

a panty (10) made of fabric and having an upper section defining a waist opening (15), and having a lower section defining a pair of leg openings (13 and 14) and having a crotch section intermediate said pair of leg openings;

a first elastic binding affixed to said panty about said waist opening;

a second elastic binding affixed to said panty about one of said pair of leg openings;

a third elastic binding affixed to said panty about the other of said pair of leg openings;

a panty liner (11) made of a flexible vinyl backed terry cloth and having a rectangular configuration with a pair of concave cutouts (20 and 21) with each one of said pair of concave cutouts being affixed about a respective one of said pair of leg opening, and having a back section (22) which extends from said waist opening down to said crotch section to form a substantially liquid-proof back liner extending across a substantial rear portion of said panty, and having a front section (24) which extends from said waist opening down to said crotch section to form a substantially liquid-proof front liner extending across a substantial front portion of said panty, and having a crotch (section) member (23) to form a substantially liquid-proof crotch portion of said panty liner, said panty liner being stitched about its periphery into said panty with an overcast stretch stitch (30) to facilitate flexibility and wearing with the terry cloth facing inwardly and the flexible vinyl facing said panty, said panty liner being dimensioned for having an upper rear edge portion (26) of said back section extending approximately to and along a predetermined rear portion of the waist opening of said panty and for having a front edge portion (25) of said front section extending approximately to and along a predetermined front portion of the waist opening of said panty.

2. A panty construction as in claim 1, wherein:
the panty liner is formed from a sheet of SYNTILON type material.

3. A panty as in claim 1, wherein:
the upper rear edge portion (26) and the front edge portion (25) of said panty liner are affixed about a peripheral portion of the upper section of said panty defining the waist opening; and
the concave cutouts are each affixed to the lower section about a peripheral portion of a respective one of said pair of leg openings.

* * * * *